United States Patent [19]

Stewart

[11] Patent Number: 5,518,712
[45] Date of Patent: May 21, 1996

[54] WATER RESISTANT SUNSCREEN PROTECTION AND INSECT REPELLENT COMPOUND

[76] Inventor: Ernest Stewart, 101 W. Club Dr., Thomasville, Ga. 31792

[21] Appl. No.: 154,584

[22] Filed: Nov. 18, 1993

Related U.S. Application Data

[63] Continuation-in-part of Ser. No. 904,514, Jun. 25, 1992.

[51] Int. Cl.$^6$ .......................................... A61K 7/42
[52] U.S. Cl. ................................ 424/59; 514/844
[58] Field of Search ...................... 424/59; 514/844

[56] References Cited

U.S. PATENT DOCUMENTS

| | | | |
|---|---|---|---|
| 2,356,801 | 8/1944 | Travis et al. | 424/DIG. 10 |
| 2,435,005 | 1/1948 | Huppke et al. | 424/60 |
| 2,853,423 | 9/1958 | La Via | 424/60 |
| 3,821,363 | 6/1974 | Black et al. | 424/60 |
| 3,970,584 | 7/1976 | Hart et al. | 424/45 |
| 4,083,966 | 4/1978 | Bowell | 424/DIG. 10 |
| 4,268,498 | 5/1981 | Gedeon et al. | 424/59 |
| 4,477,467 | 10/1984 | Nishizawa et al. | 424/DIG. 10 |
| 5,093,107 | 3/1992 | Matravers | 424/60 |

OTHER PUBLICATIONS

Chem. Abs., vol. 112:164746, Abstract of French Pat. No. 2622103 (Apr. 28, 1989), Thorel.
Chem. Abs., vol. 103:191489, Abstract of Hungarian Pat. No. 35151 (Jun. 28, 1985), Erdos.

*Primary Examiner*—Shelley A. Dodson
*Assistant Examiner*—Michael A. Williamson
*Attorney, Agent, or Firm*—Franklin J. Cona

[57] ABSTRACT

An improved sunscreen protection and insect repellent combination compound having an SPF factor of 15 and further having an unexpected unusually long efficacy period when used in rainy conditions and prolonged periods of high humidity as in tropical and sub-tropical rain forests or the like, and in underwater conditions as in swimming. The compound forms a lotion that is easy to store. The lotion can be applied to the skin of a person with little or no training. No special precautions are required by the person when applying the lotion. The compound has a sweet taste when applied to the lips and is pleasantly scented. The compound forms a thin film on the skin, but is non-greasy to the touch. The lotion is easily removed by scrubbing with soap and water. The sunscreen component being about between 4% to 8% by weight, the insect repellent compound being about between 12% to 22% by weight, and the water based solvent being about between 27% to 37% by weight.

7 Claims, No Drawings

WATER RESISTANT SUNSCREEN PROTECTION AND INSECT REPELLENT COMPOUND

This is a Continuation-In-Part of application Ser. No. 07/904,514 filed Jun. 25, 1992.

BACKGROUND OF THE INVENTION

1. Field of the Invention

This invention relates to a synergistic compound for sunscreen protection and insect repellent compound, and in particular an improved water resistant combination sunscreen protection and insect repellent compound. The compound is nongreasy, pleasant smelling, and sweet tasting with an approximate SPF factor of 15. Although the compound is highly water resistant, it is easily removed with soap and water and scrubbing.

2. Description of the Background Art

Insect borne diseases are a major non-battle injury threat to the military. Seven of the top 11 diseases that reduce military effectiveness are transmitted by insects. It is imperative for peak military operational efficiency that an acceptable insect repellent be produced to reduce the disease threat and to provide personal protection from insect borne diseases. The insect repellent compound must also meet the unique requirements necessary for personal protection of the armed forces. When considering the broad spectrum of use, the repellent should be long lasting and acceptable to the user. Also, the military spends long periods of time outdoors and accordingly, an acceptable sunscreen protectant/insect repellent combination compound for use by field military personnel is highly desirable, particularly if it is compatible with other military materials, such as clothing and weapons. In other words, the compound should not have a negative effect on uniforms or the use and operation of weapons.

The military services have not developed a satisfactory sunscreen protectant/insect repellant compound that meet their unique operating needs.

A second major need exists for people who live and work and play in the outdoors. They have protected themselves from insects for years by using insect repellent compounds. Likewise, people who live and play and work outdoors have used suntan compounds to accelerate the darkening of the exposed skin. Only recently the knowledge of the adverse effects of the suns' ultra violet rays causing skin cancer has caused people to switch from suntan lotions to sunscreening lotions that provide protection from the sun. Those lotions are measured on a scale of increasing protection from 1 to 33. The scale is called the "SPF" or sun protection factor. The factor allows the consumer to determine the degree of sunburn that one is willing to accept for a given period of time in the direct rays of the suns' ultra violet rays.

Many civilian products have become commercially available in the recent past that combine sunscreen protection lotions and insect repellent lotions in one package. These products, for many reasons, are not completely satisfactory. Among the reasons why they are not satisfactory are:

First, the insect repellent compounds available are greasy, have a foul odor, and are usually effective for short periods and require the person to continuously apply the lotion to maintain the desired degree of insect repellency on the skin. In many cases, as for example, in a duck blind this is very inconvenient because the person can not repeatedly apply the insect repellent lotion and maintain perfect stillness in the duck blind.

Second, many combination insect repellent and sunscreen protection compounds are easily removed with water. This is a particular problem in the summertime when the person sweats. The effectiveness of the insect repellent and sunscreen protection lotion is dramatically reduced due to sweat removing the compound from the skin.

Third, most insect repellent compounds are oily and offensive to the olfactory systems of the wearer as well as people around the wearer. Also, the heaviness in the material is an impediment to the function of the sweat glands and could cause discomfort to the wearer.

Fourth, the preparations commercially available today are not truly cosmetic in that they do not enhance the appearance and the texture of the skin.

Fifth, most sunscreen protectant compounds have a bitter taste when applied to skin around the lips.

U.S. Pat. No. 1,471,344 issued to Loudin discloses a insect repellent composition which mixes equal parts of PHENYL SALICYLATE and camphor.

U.S. Pat. No. 3,186,912 issued to Beamer discloses a cosmetic emulsion having sunscreening and insect repellent properties.

U.S. Pat. No. 4,529,598 issued to Wong discloses an insect repellent compound which can be used as a sole active component or in an admixture with other compounds having a different utility. The invention further discloses the compound may be incorporated into a cream, lotion, powder or a suntan oil.

U.S. Pat. No. 2,170,185 issued to Carpenter discloses a suntan cream having methyl anthranilate which is a methyl ester of anthranilic acid.

U.S. Pat. No. 4,434,154 issued to McShane discloses a tanning and screening compound that is highly stable after prolonged storage. The compound is useful even after prolonged storage for shielding human skin from the harmful ultra violet rays of the sun.

U.S. Pat. No. 4,701,321 issued to Bernstein discloses a liquid detergent with a sunscreen agent selected from the aminobenzoic acid family the other components of the composition being a preservative, a non-ionic detergent, an amphoteric detergent, or a mixture thereof in a aqueous vehicle.

U.S. Pat. No. 4,820,508 issued to Wortzman discloses a skin protective composition for topical application to protect human skin from infrared radiation. The invention contains titanium dioxide and mica or coated mica as its' principal active reagents.

U.S. Pat. No. 4,756,905 issued to Melnik discloses a composition for repelling insects and camouflaging the human skin. The insect repellent, N or N-DIETHYL-M-TOLUAMIDE and a camouflage pigment is combined along with an emulsifier to allow a single application to serve both functions.

U.S. Pat. No. 3,590,118 issued to Conrady, et al discloses a long lasting insect repellent film for skin application. The active chemical agents are dissolved in interpolymer resigns to provide a slow release system for the active chemical agents when spread and dried as a film on a human being. The coating can be applied by spraying or spreading and is easily removable with a soapy water solution.

None of these previous efforts, however, provide the benefits intended with the present invention. Additionally, prior techniques do not suggest, the present inventive combination of component elements as disclosed and claimed herein. The present invention achieves its intended purposes, objectives and advantages over the prior art devices through a new, useful and unobvious combination of component elements, which is simple to use, with the utilization of a minimum number of functioning ingredients, at a reasonable cost to manufacture, test, package and by employing only readily available materials.

Accordingly, it is an object of the invention to provide a combination sunscreen protection and insect repellent product that meet the broad spectrum of use for military personnel.

It is an object of the invention to provide a combination sunscreen protection and insect repellent product that contributes to the effectiveness of the military by reducing insect borne disease among military personnel.

It is another object of the invention to provide a combination sunscreen protection and insect repellent product that is resistant to breakdown by water, but is readily removed by soap and water and mild scrubbing.

It is an object of the invention to provide a combination sunscreen protection and insect repellent product that It is a further object of the invention to provide a combination sunscreen protection and insect repellent product that is not greasy to the touch, pleasant smelling to the wearer, sweet tasting when applied to skin close to the lips, and nonoffensive to those people around the wearer.

It is a still further object of the invention to provide a combination sunscreen protection and insect repellent product that does not impede the natural function of the wearers' sweat glands.

It is a further important object of the invention to provide a combination sunscreen protection and insect repellent product that enhances the appearance and feel of the wearers' skin.

It is a final important object of the invention to provide a combination sunscreen protection and insect repellent product that is long lasting and does not require frequent reapplication to maintain its effectiveness.

Although there have been many inventions related to sunscreen protection and insect repellent compounds, none of the inventions have become sufficiently effective, low cost and reliable enough to become commonly used. The present invention meets the requirements of long lasting efficacy under extreme environmental conditions, low initial cost, water resistant, non-greasy, sweet tasting, ease of application, pleasing to the olfactory senses, and minimal amount of instruction to successfully practice and use the invention.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiments in addition to the scope of the invention defined by the claims.

SUMMARY OF THE INVENTION

For the purpose of summarizing the invention, the invention may be incorporated into a synergistic sunscreen protection and insect repellent compound having an extremely long efficacy period when used in rainy conditions and prolonged periods of high humidity as in tropical and sub-tropical rain forests, and even underwater. The compound comprises a sunscreen constituent constituting about between 4% to 8% by weight of the compound, an insect repellent constituent constituting about between 12% to 22% by weight of the compound, a plurality of ingredients contributing the synergistically long efficacy attribute, and the balance being composed of a water based solvent comprising about between 27% to 37% by weight of the compound.

The compound forms a lotion that is easy to store. The lotion can be applied to the skin of a person with little or no training. No special precautions are required by the person when applying the lotion. When applied, a thin film is formed on the skin that is non-greasy to the touch and resists water, yet is readily removed by soap and water and scrubbing.

The resultant compound has an extremely long efficacy period even when subjected to extreme environmental conditions of high humidity, and even when the wearer is underwater. Further, the compound was tested exhaustively under strict laboratory and field conditions using the appropriate protocols that are approved by the U.S. Army Medical Material Development Activity.

The invention is practiced by first mixing water and propylene glycol for forming an initial mixture and heating the initial mixture to 75° C. with propeller agitation in a stainless steel kettle large enough to hold the entire batch and slowly sifting in carbopol and then Pemulen TR1. Then, seamollient and disodium EDTA are added uniformly to form a first interim mixture. The first interim mixture is mixed while maintaining the temperature in the kettle at 75° C. for 30 minutes.

Next, N,N-diethyl-M-toluamide (deet), cetearyl alcohol, octyl methoxycinnamate, octyl salicilate, peg-40 stearate (MYRJ 52S), oxybenzone (sunscreen), tricontonyl PVP (Ganex WP-660), and vitamin E acetate are combined in a second initial mixture with slow agitation in a second stainless steel kettle and heated to 85° C. The ingredients in the second kettle are mixed for 30 minutes while maintaining the temperature. After 30 minutes has elapsed, the second initial mixture in the second kettle is added to the interim mixture in the first kettle and a second interim mixture is formed. The second interim mixture is mixed for 30 minutes. Then, triethanolamine is added to the second interim mixture in the first kettle using a slow sidesweep agitation to produce a third interim mixture. The third interim mixture in the first kettle is mixed for 30 minutes while maintaining the temperature at 75° C. Then, the third interim mixture in the first kettle is cooled to 45° C. while stirring slowly. Citronella, fragrance, saccharin and germaben II are then slowly added to the third interim mixture in the first kettle to produce a resultant mixture.

The resultant mixture in the first kettle is mixed for 20 minutes to provide uniformity and then the resultant mixture is passed through a Gifford-Wood colloid mill with a narrow setting for providing a small particle size. The resultant mixture is recirculated in the first kettle until homogeneity is achieved and at this point, the resultant mixture is ready for packaging.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent structures do not depart from the spirit and scope of the invention as set forth in the appended claims.

DETAILED DESCRIPTION OF THE PREFERRED EMBODIMENT

The present invention, Example 1, is prepared using the components in Phases A, B, C, D, E and F respectively. The resulting compound that is produced in accordance with the present invention has the desired characteristics of providing a nongreasy, pleasant smelling, insect repellent and a sweet tasting sunscreen protectant with an approximate SPF of 15. The compound forms a lotion that is easy to store. The lotion can be applied to the skin of a person with little or no training. No special precautions are required by the person when applying the lotion. Further, the resultant compound has the synergistic attribute of an extremely long efficacy period when used in rainy conditions and prolonged periods of high humidity as in tropical and sub-tropical rain forests or the like, or when the wearer is underwater. The compound forms a thin film on the skin which resists water, yet is readily removed by soap and water and scrubbing.

The compound was evaluated under appropriate protocols for measuring the efficacy of sunscreen formulations and insect repellent formulations against mosquitos. Cage tests were conducted at Walter Reed Army Hospital. Then, the compound was tested under strict field conditions using appropriate protocols that are approved by the U.S. Army Medical Material Development Activity. The field tests were conducted at the U.S. Army testing facilities in Alaska, Thailand, and South America.

Immersion tests were conducted to determine the waterproofing effectiveness of the compound. Five test subjects were immersed in a whirlpool for a total of eighty (80) minutes. The initial SPF factor prior to immersion was 16.1. Measurements were taken at 20 minute intervals on all 5 test subjects. The interim SPF factor and final SPF factor was 16.1 in all cases. Additional tests are planned with longer durations to confirm the original results and to probe for the upper limit of the waterproofing effectiveness of the invention.

The practice of the invention results in a composition as shown below in Example I, with the ingredients being representative of their constituent percentages by weight percent.

EXAMPLE I

|  | WEIGHT % |
|---|---|
| PHASE A | |
| Deionized Water | 32.53 |
| Propylene Glycol | 2.50 |
| Carbopol 940 (2% Soln) | 5.00 |
| Pemulen TR1 | 15.00 |
| Seamollient | 1.00 |
| Tetrasodium EDTA | 0.10 |
| PHASE B | |
| N,N-diethyl-M-toluamide (Deet) | 17.00 |
| Cetearyl Alcohol | 3.50 |
| Octyl Methoxycinnamate (Neoheliopan AV) | 7.50 |
| Octyl Salicate (Neoheliopan OS) | 5.00 |
| Peg 40 Sterate (MYRJ 52S) | 0.15 |
| Sunscreen (Benzophenone-3) | 6.00 |
| Tricontonyl PVP (Ganex WP-660) | 3.00 |
| Vitamin E Acetate | 0.25 |
| PHASE C | |
| Triethanolamine 99% | 0.11 |
| PHASE D | |
| Citronella Java | 0.01 |
| Fragrance MF 3871 | 0.25 |
| PHASE E | |
| Sodium Saccharin | 0.10 |
| PHASE F | |
| Germaben II | 1.00 |

The mixing is done in a conventional manner and the ingredients in each phase are mixed in the sequence described hereinbelow. The choice of the particular material used dictates the mixing time and temperature change rates.

The composition of the sunscreen component comprises from about between 4% to 8% by weight of the composition. The composition of the insect repellent component comprises from about between 12% to 22% by weight of the composition. The composition of the water based filler comprises from about between 27% to 37% by weight of the composition. The balance of the composition comprises agents commonly used as ingredients to produced qualities such as fragrance, color and sweet taste.

When a person applies the compound outlined in Example 1 to the exposed parts of the body, according to the method disclosed herewith, a thin film forms on the skin that provides a non-greasy, pleasant smelling insect repellent and a sweet tasting sunscreen protectant. The compound has the unexpected property of extremely long efficacy even when subjected to extreme temperature and humidity, and even when the exposed body parts are underwater for extended periods of time. The synergistic result of combining Pemulen TR1, MYRJ 52S (Peg 40 Sterate), and Ganex WP-660 (Tricontonyl PVP) in the quantities disclosed in Example 1, and preparing the compound according to the steps disclosed herein provide the invention with unexpected superior insect repellent and sunscreen properties.

Pemulen TR1 is a known emulsifier/stabilizer. The product is made by the B. F. Goodrich company in Akron, Ohio. Predominantly, it is known for it's emulsion/stabilization quality. Typically, Pemulen TR1 is used in perfumes and hair glossing and elegant skin care moisturizer applications.

MYRJ 52S is a non-ionic oil and water emulsifier. It is manufactured by the ICI Corporation in Wilmington, Del. Primarily, MYRJ 52S is known for its emulsification qualities. Typically, MYRJ 52S is used for general skin formulations including facial lotions and skin moisturizers and the like.

Ganex WP660 is a film-forming waterproof agent manufactured by the ISP Corporation (International Specialty Products) of Wayne, N.J. Primarily, it is used for quality waterproofing sunscreen formulations.

The combination of MYRJ 52S, Pemulen TR1, Ganex WP660, Benzophene-3 (sunscreen) and N, N-Diethyl-M-Toluamide (DEET) would not normally be expected to form an emulsion when combined. However, by combining them in the ratios disclosed, a stable emulsion is formed. This emulsion when rubbed onto the skin "breaks down" as the Pemulen is precipitated by the salt on the skin and the emulsion breaks. There is now insufficient emulsifier left on the skin to wash off when sweating or swimming. Additionally, the Ganex WP660 combines with the DEET and the sunscreen to form a uniform thick sunscreen film which is waterproof. The increased thickness of the film allows for enhanced SPF performance since the optical path length of the UV radiation have now increased and thus the sunscreen absorbs the UV more efficiently.

The prior art does not reveal nor even suggest a motivation for combining the above cited ingredients. The inventor experimented with various compounds hoping to develop the invention. It was only after numerous failed attempts, that the invention was finally achieved. Cage tests were conducted at W. Reed U.S. Army hospital and were followed by exhaustive trials under actual field conditions with extreme temperature and humidity. The field trials were conducted by the U.S. Army Medical Material Development Activity, Office of Research and Technology Applications, at their test facilities in Alaska, Thailand, and South America. The results confirmed the disclosed and claimed synergistic increase in efficacy beyond dispute. The results of the cage tests and field trials will be submitted by Preliminary Amendment as soon as the U.S. Army Office of Research and Technology Applications releases the data to the inventor.

The underwater tests were conducted in a whirlpool with a person having the invention applied to their skin. There were a total of five test subjects in the whirlpool with the invention applied on their skin. The subjects were emersed in the whirlpool which was under extreme agitation and were removed from the whirlpool at 20 minute intervals to measure the SPF factor. Test results show that the SPF factor was 16.1 upon initial immersion and 16.1 after 80 minutes or four measurement observations. The SPF factor of the compound showed absolutely no degradation whatsoever. The immersion tests were terminated at that time as lack of degradation indicated that the SPF factor of the invention would last well beyond the target spectrum of three hours. The immersion tests conducted by the U.S. Army Office of Research and Technology Application Personnel at Walter Reed Army Hospital in Washington, D.C., indicates that the SPF factor is unaffected after exposure underwater.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of structures and the combination of individual ingredients may be resorted to without departing from the spirit and scope of the invention.

Now that the invention has been described,
What is claimed is:

1. A stable emulsion composition which functions as a sweet tasting waterproof sunscreen protectant and non-greasy, pleasant smelling insect repellent having an extremely long efficacy period when used by a person in rainy conditions and prolonged periods of high humidity as in tropical and sub-tropical rain forests comprising in combination:

a first constituent functioning as a sunscreen and constituting from about between 4% to 8% by weight of the composition;

a second constituent of N-N-diethyl-M-toluamide functioning as an insect repellent constituting about between 12% to 22% of the composition;

a third constituent functioning as a water based solvent constituting about between 27% to 37% by weight of the composition;

a fourth constituent functioning as a sweetener constituting about between 0.05% to 0.15% by weight of the composition;

a fifth constituent functioning as a pleasant scent material constituting about between 0.2% to 0.3% by weight of the composition; and a sixth constituent of Tricontonyl PVP of about between 2% to 4% by weight of the composition for forming a thin film when applied to the skin of the person for remaining on the skin when submerged underwater for long periods of time of about between 1 to 1.25 hours, the thin film further being non-greasy to the touch and still further retaining an SPF factor of 15 when submerged underwater for long periods of time of about between 1 to 1.25 hours.

2. A method for formulating a stable emulsion composition which functions as a sunscreen protectant and insect repellent having an extremely long efficacy period when used by a person in rainy conditions and prolonged periods of high humidity as in tropical and sub-tropical rain forests comprising the steps of:

combining water and propylene glycol with propeller agitation in a first stainless steel kettle for forming an initial mixture, the kettle being large enough to hold an entire volume of the composition;

heating the initial mixture to 75° C.;

slowly sifting in carbopol and then Pemulen TR1;

adding seamollient and disodium EDTA uniformly for forming an interim mixture;

maintaining the temperature of the interim mixture in the first kettle at 75° C. for 30 minutes;

combining N,N-diethyltoluamide, cetearyl alcohol, octyl methoxycinnamate, octyl salicilate, peg-40 stearate, oxybenzone, tricontonyl PVP, and vitamin E acetate with slow agitation for forming a second initial mixture in a second stainless steel kettle;

heating the second initial mixture to 85° C.;

maintaining the temperature of the second initial mixture in the second kettle for 30 minutes;

adding the second initial mixture in the second kettle uniformly to the interim mixture in the first kettle for forming a second interim mixture;

mixing the second interim mixture in the first kettle for 30 minutes;

adding triethanolamine to the second interim mixture in the first kettle using slow sidesweep agitation for forming a third interim mixture;

mixing the third interim mixture in the first kettle for 30 minutes while maintaining the temperature at 75° C.

cooling the third interim mixture in the first kettle to 45° C. while stirring slowly;

slowly adding citronella, fragrance, saccharin and germaben II to the third interim mixture in the first kettle for forming a resultant mixture;

mixing the resultant mixture in the first kettle for 20 minutes for providing uniformity;

passing the resultant mixture in the first kettle through a Gifford-Wood colloid mill with a narrow setting for providing a small particle size;

recirculating the resultant mixture in the first kettle until homogeneity is achieved; and packaging the resultant mixture.

3. The composition as set forth in claim 1 wherein the major component of the first constituent is benzophene-3.

4. The composition as set forth in claim 1 wherein the principal component of the third constituent is distilled water.

5. A composition as recited in claim 1 wherein the principal component of the fourth constituent is sodium saccharin.

6. A composition as recited in claim 1 wherein the principal components of the fifth constituent are citronella and fragrance MF 3871.

7. A method of applying the composition as set forth in claim 1 to an exposed portion of a person's body for functioning as a sunscreen protectant and insect repellent having an extremely long efficacy period when used by a person in rainy conditions and prolonged periods of high humidity as in tropical and sub-tropical rain forests, comprising the steps of:

agitating the composition by shaking until the composition is homogenous; and pouring the homogenous composition onto an applicator and then coating the exposed portions of the body with the homogenous composition.

* * * * *